US006764684B2

(12) United States Patent
Saitoh et al.

(10) Patent No.: US 6,764,684 B2
(45) Date of Patent: Jul. 20, 2004

(54) AVIAN HERPESVIRUS-BASED RECOMBINANT INFECTIOUS BURSAL DISEASE VACCINE

(75) Inventors: Shuji Saitoh, Kanagawa (JP); Takashi Okuda, Tokyo (JP); Mayumi Kubomura, Kanagawa (JP); Kristi M. Moore, Lenexa, KS (US)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 09/964,895

(22) Filed: Sep. 28, 2001

(65) Prior Publication Data

US 2003/0099667 A1 May 29, 2003

(51) Int. Cl.[7] ............................................... A61K 39/12
(52) U.S. Cl. ................ 424/199.1; 424/816; 424/204.1; 435/69.1; 435/320.1; 435/91.1
(58) Field of Search .......................... 424/199.1, 204.1, 424/816; 435/320.1, 91.1, 91.33, 69.1; 536/24.1, 23.72

(56) References Cited

U.S. PATENT DOCUMENTS

| | | | |
|---|---|---|---|
| 5,350,575 A | 9/1994 | Azad et al. | 424/192.1 |
| 5,595,912 A | 1/1997 | Vakharia et al. | 435/320.1 |
| 5,733,554 A | 3/1998 | Audonnet et al. | 424/199.1 |
| 5,834,305 A | 11/1998 | Cochran et al. | 435/320.1 |
| 5,849,575 A | 12/1998 | Azad et al. | 435/320.1 |
| 5,853,733 A | 12/1998 | Cochran et al. | 424/199.1 |
| 5,928,648 A | 7/1999 | Cochran | 424/199.1 |
| 5,961,982 A | 10/1999 | Cochran | 424/199.1 |
| 5,980,906 A * | 11/1999 | Audonnet et al. | 424/199.1 |
| 6,013,261 A | 1/2000 | Sonoda et al. | 424/199.1 |

FOREIGN PATENT DOCUMENTS

| | | |
|---|---|---|
| EP | 1 026 246 A1 | 8/2000 |
| WO | WO 87/04463 | 7/1987 |
| WO | WO 89/01040 | 3/1989 |
| WO | WO 91/16925 | 11/1991 |
| WO | WO 93/25665 | 12/1993 |
| WO | WO 96/05291 | 2/1996 |
| WO | WO 99/18215 | 4/1999 |

OTHER PUBLICATIONS

Specification of USSN 09/509,871, filed Jul. 5, 2001. This document represents a translation of WO99/18215.
T. A. Kost, et al.; "The Nucleotide Sequence of the Chick Cytoplasmic β–actin Gene"; Nucleic Acids Research; vol. 11: No. 23; pp. 8287–8301 (1983).
A.A. Azad et al.; "Deletion Mapping and Expression in Escherichia coli of the Large Genomic Segment of a Birnavirus"; Virology; 161, pp. 145–152 (1987).

F.S.B. Kibenge, et al.; "Nucleotide Sequence Analysis of Genome Segment A of Infectious Bursal Disease Virus"; Journal of General Virology; 71, pp. 569–577 (1990).
K. J. Fahey, et al.; "Characterization by Western Blotting of the Immunogens of Infectious Bursal Disease Virus"; J. Gen. Virol.; vol. 66, pp. 1479–1488; 1985.
Hans–Georg Heine, et al.; "Sequence analysis and expression of the host–protective immunogen VP2 of a variant strain of infectious bursal disease virus which can circumvent vaccination with standard type I strains"; Journal of General Virology (1991), 72, pp. 1835–1843.
Michael D. Brown et al.; "VP2 sequences of recent European 'very virulent' isolates of infectious bursal disease virus are closely related to each other but are distinct form those of 'Classical' strains"; Journal of General Virology (1994), 75, pp. 675–680.
Raphaël Darteil, et al.; "Herpesvirus of Turkey Recombinant Viruses Expressing Infectious Bursal Disease Virus (IBDV) VP2 Immunogen Induce Protection against an IBDV Virulent Challenge in Chickens"; Virology, 211, pp. 481–490 (1995).
T.V. Dormitorio et al.; "Sequence Comparisons of the Variable VP2 Region of Eight Infectious Vursal Disease Virus Isolates"; Avian Diseases; 41, pp. 36–44; 1997.
Y. C. Cao, et al.; "Molecular Characterization of Seven Chinese Isolates of Infectious Bursal Disease Virus: Classical, Very Virulent, and Variant Strains"; Avian Disease; 42; pp. 340–351, 1998.
Kenji Tsukamoto et al.; Protection of Chickens against Very Virulent Infectious Bursal Disease Virus (IBDV) and Marek's Disease Virus (MDV) with a Recombinant MDV Expressing IBDV VP2; Virology 257, pp. 352–362; 1999.
X. Liu, et al.; "Simplified Sample Processing Combined with a Sensitive Nested Polymerase Chain Reaction Assay for Detection of Infectious Bursal Disease Virus in the Bursa of Fabricus"; Avian Diseases, 42; pp. 480–485, 1998.

* cited by examiner

Primary Examiner—Ali R. Salimi
(74) Attorney, Agent, or Firm—Armstrong, Kratz, Quintos, Hanson & Brooks, LLP

(57) ABSTRACT

The present invention provides an avian recombinant herpesvirus modified by the presence of the cDNA encoding the VP2 of the Delaware Variant E strain of IBDV, a subtype of IBDV serotype 1 strains. The present invention further provides an avian recombinant herpesvirus comprised of the VP2 gene, of which the backbone virus is a Marek's disease vaccine strain, such as herpesvirus of turkeys. A poultry vaccine including the avian herpes recombinant virus described in the present invention can induce in chickens protective immunity against a variety of different subtypes of IBDV.

4 Claims, 5 Drawing Sheets

SEQUENCE LISTING

```
<160> NUMBER OF SEQ ID NOS: 27

<210> SEQ ID NO 1
<211> LENGTH: 1374
<212> TYPE: DNA
<213> ORGANISM: Infectious bursal disease virus
<220> FEATURE:
<221> NAME/KEY: CDS
<222> LOCATION: (7)..(1368)
<223> OTHER INFORMATION: product: VP2 of IBDV E strain

<400> SEQUENCE: 1 tctaga atg aca aac ctg tca gat caa acc caa cag att gtt ccg ttc       48
```

-continued

```
            Met Thr Asn Leu Ser Asp Gln Thr Gln Gln Ile Val Pro Phe
             1               5                  10 ata cgg agc ctt ctg atg cca aca acc gga ccg gcg tcc att ccg gac    96
Ile Arg Ser Leu Leu Met Pro Thr Thr Gly Pro Ala Ser Ile Pro Asp
 15              20                  25                  30 gac acc ctg gag aag cac act ctc agg tca gag acc tcg acc tac aat   144
Asp Thr Leu Glu Lys His Thr Leu Arg Ser Glu Thr Ser Thr Tyr Asn
                 35                  40                  45 ttg act gtg ggg gac aca ggg tca ggg cta att gtc ttt ttc cct gga   192
Leu Thr Val Gly Asp Thr Gly Ser Gly Leu Ile Val Phe Phe Pro Gly
                     50                  55                  60 ttc cct ggc tca att gtg ggt gct cac tac aca ctg cag agc aat ggg   240
Phe Pro Gly Ser Ile Val Gly Ala His Tyr Thr Leu Gln Ser Asn Gly
                         65                  70                  75 aac tac aag ttc gat cag atg ctc ctg act gcc cag aac cta ccg gcc   288
Asn Tyr Lys Phe Asp Gln Met Leu Leu Thr Ala Gln Asn Leu Pro Ala
             80                  85                  90 agc tac aac tac tgc agg cta gtg agt cgg agt ctc aca gta agg tca   336
Ser Tyr Asn Tyr Cys Arg Leu Val Ser Arg Ser Leu Thr Val Arg Ser
 95                 100                 105                 110 agc aca ctc cct ggt ggc gtt tat gca cta aac ggc acc ata aac gcc   384
Ser Thr Leu Pro Gly Gly Val Tyr Ala Leu Asn Gly Thr Ile Asn Ala
                115                 120                 125 gtg acc ttc caa gga agc ctg agt gaa ctg aca gat gtt agc tac aac   432
Val Thr Phe Gln Gly Ser Leu Ser Glu Leu Thr Asp Val Ser Tyr Asn
                130                 135                 140 ggg ttg atg tct gca aca gcc aac atc aac gac aaa att ggg aac gtc   480
Gly Leu Met Ser Ala Thr Ala Asn Ile Asn Asp Lys Ile Gly Asn Val
            145                 150                 155 cta gta ggg gaa ggg gta acc gtc ctc agc tta ccc aca tca tat gat   528
Leu Val Gly Glu Gly Val Thr Val Leu Ser Leu Pro Thr Ser Tyr Asp
            160                 165                 170 ctt ggg tat gtg agg ctt ggt gac ccc ata ccc gct ata ggg ctt gac   576
Leu Gly Tyr Val Arg Leu Gly Asp Pro Ile Pro Ala Ile Gly Leu Asp
175                 180                 185                 190 cca aaa atg gta gca aca tgt gac agc agt gac agg ccc aga gtc tac   624
Pro Lys Met Val Ala Thr Cys Asp Ser Ser Asp Arg Pro Arg Val Tyr
                195                 200                 205 acc ata act gca gcc gat aat tac caa ttc tca tca cag tac caa aca   672
Thr Ile Thr Ala Ala Asp Asn Tyr Gln Phe Ser Ser Gln Tyr Gln Thr
                210                 215                 220 ggt ggg gta aca atc aca ctg ttc tca gcc aac att gat gcc atc aca   720
Gly Gly Val Thr Ile Thr Leu Phe Ser Ala Asn Ile Asp Ala Ile Thr
            225                 230                 235 agt ctc agc gtt ggg gga gag ctc gtg ttc aaa aca agc gtc caa agc   768
Ser Leu Ser Val Gly Gly Glu Leu Val Phe Lys Thr Ser Val Gln Ser
            240                 245                 250 ctt gta ctg ggc gcc acc atc tac ctt ata ggc ttt gat ggg act gcg   816
Leu Val Leu Gly Ala Thr Ile Tyr Leu Ile Gly Phe Asp Gly Thr Ala
255                 260                 265                 270 gta atc acc aga gct gtg gcc gca aac aat ggg ctg acg gcc ggc atc   864
Val Ile Thr Arg Ala Val Ala Ala Asn Asn Gly Leu Thr Ala Gly Ile
                275                 280                 285 gac aat ctt atg cca ttc aat ctt gtg att cca acc aat gag ata acc   912
Asp Asn Leu Met Pro Phe Asn Leu Val Ile Pro Thr Asn Glu Ile Thr
                290                 295                 300 cag cca atc aca tcc atc aaa ctg gag ata gtg acc tcc aaa agt gat   960
Gln Pro Ile Thr Ser Ile Lys Leu Glu Ile Val Thr Ser Lys Ser Asp
            305                 310                 315
```

-continued

```
ggt cag gca ggg gaa cag atg tca tgg tcg gca agt ggg agc cta gca    1008
Gly Gln Ala Gly Glu Gln Met Ser Trp Ser Ala Ser Gly Ser Leu Ala
320                 325                 330 gtg acg atc cat ggt ggc aac tat cca gga gcc ctc cgt ccc gtc aca    1056
Val Thr Ile His Gly Gly Asn Tyr Pro Gly Ala Leu Arg Pro Val Thr
335                 340                 345                 350 cta gtg gcc tac gaa aga gtg gca aca gga tct gtc gtt acg gtc gct    1104
Leu Val Ala Tyr Glu Arg Val Ala Thr Gly Ser Val Val Thr Val Ala
            355                 360                 365 ggg gtg agc aac ttc gag ctg atc cca aat cct gaa cta gca aag aac    1152
Gly Val Ser Asn Phe Glu Leu Ile Pro Asn Pro Glu Leu Ala Lys Asn
        370                 375                 380 ctg gtt aca gaa tac ggc cga ttt gac cca gga gcc atg aac tac acg    1200
Leu Val Thr Glu Tyr Gly Arg Phe Asp Pro Gly Ala Met Asn Tyr Thr
    385                 390                 395 aaa ttg ata ctg agt gag agg gac cgc ctt ggc atc aag acc gtc tgg    1248
Lys Leu Ile Leu Ser Glu Arg Asp Arg Leu Gly Ile Lys Thr Val Trp
400                 405                 410 cca aca agg gag tac act gac ttt cgt gag tac ttc atg gag gtg gcc    1296
Pro Thr Arg Glu Tyr Thr Asp Phe Arg Glu Tyr Phe Met Glu Val Ala
415                 420                 425                 430 gac ctc aac tct ccc ctg aag att gca gga gca ttt ggc ttc aaa gac    1344
Asp Leu Asn Ser Pro Leu Lys Ile Ala Gly Ala Phe Gly Phe Lys Asp
            435                 440                 445 ata atc cgg gcc ata agg agg tgagtcgac                              1374
Ile Ile Arg Ala Ile Arg Arg
            450
```

<210> SEQ ID NO 2
<211> LENGTH: 453
<212> TYPE: PRT
<213> ORGANISM: Infectious bursal disease virus

<400> SEQUENCE: 2

```
Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190
```

```
Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
        210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Asp Gly Gln
305                 310                 315                 320

Ala Gly Glu Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450

<210> SEQ ID NO 3
<211> LENGTH: 1525
<212> TYPE: DNA
<213> ORGANISM: Gallus gallus
<220> FEATURE:
<221> NAME/KEY: promoter
<222> LOCATION: (21)..(1505)

<400> SEQUENCE: 3
ctgcagctca gtgcatgcac gctcattgcc catcgctatc cctgcctctc ctgctggcgc     60
tccccgggag gtgacttcaa ggggaccgca ggaccacctc gggggtgggg ggagggctgc    120
acacgcggac cccgctcccc ctccccaaca aagcactgtg gaatcaaaaa ggggggaggg    180
gggatggagg ggcgcgtcac accccgccc cacaccctca cctcgaggtg agccccacgt     240
tctgcttcac tctccccatc tccccccct cccaccccc aatttttgtat ttatttattt    300 tttaattatt ttgtgcagcg atgggggcgg gggggggggg ggcgcgcgcc aggcggggcg    360
ggcgggggcc aggggcgggg cggggcgagg cggagaggtg cggcggcagc caatcagagc    420
ggcgcgctcc gaaagtttcc ttttatggcg aggcggcggc ggcggcggcc ctataaaaag    480
```

-continued

```
cgaagcgcgc ggcgggcggg agtcgctgcg cgctgccttc gccccgtgcc ccgctccgcc      540
gccgcctcgc gccgcccgcc ccggctctga ctgaccgcgt tactcccaca ggtgagcggg      600
cgggacggcc cttctcctcc gggctgtaat tagcgcttgg tttaatgacg gctcgtttct      660
tttctgtggc tgcgtgaaag ccttaaaggg ctccgggagg gcctttgtg cgggggggag       720 cggctcgggg ggtgcgtgcg tgtgtgtgtg cgtggggagc gccgcgtgcg gctccgcgct      780 gccgccggc tgtgagcgct gcgggcgcgg cgcgggctt tgtgcgctcc gcagtgtgcg         840
cgaggggagc gcggccgggg gcggtgcccc gcggtgcggg ggggctgcg agggaacaa        900 aggctgcgtg cggggtgtgt gcgtgggggg gtgagcaggg ggtgtgggcg cggcggtcgg     960
gctgtaaccc ccccctgcac ccccctcccc gaagttgctg agcacggccc ggcttcgggt     1020
gcggggctcc gtgcggggcg tggcgcgggg ctcgccgtgc cggcgggg gtggcggcag       1080 gtgggggtgc cgggcggggc ggggccgcct cgggccgggg agggctcggg ggaggggcgc     1140
ggcggccccc ggagcgccgg cggctgtcga ggcgcggcga gccgcagcca ttgcctttta     1200
tggtaatcgt gcgagagggc gcagggactt cctttgtccc aaatctgtgc ggagccgaaa    1260
tctgggaggc gccgccgcac ccctctagc gggcgcgggg cgaagcggtg cggcgccggc      1320
aggaaggaaa tgggcgggga gggccttcgt gcgtcgccgc gccgccgtcc ccttctccat   1380
ctccagcctc gggctgtcc gcaggggac ggctgccttc gggggggacg gggcagggcg      1440
gggttcggct tctggcgtgt gaccggcggg gtttatatct tcccttctct gttcctccgc    1500
agcccccaag cttgtcgact ctaga                                          1525

<210> SEQ ID NO 4
<211> LENGTH: 25
<212> TYPE: DNA
<213> ORGANISM: Infectious bursal disease virus

<400> SEQUENCE: 4
ctacaccttc cccaattgca tgggc                                            25

<210> SEQ ID NO 5
<211> LENGTH: 26
<212> TYPE: DNA
<213> ORGANISM: Infectious bursal disease virus

<400> SEQUENCE: 5
ggtgggaaca atgtagagac caccgg                                           26

<210> SEQ ID NO 6
<211> LENGTH: 25
<212> TYPE: DNA
<213> ORGANISM: Infectious bursal disease virus

<400> SEQUENCE: 6
atggttagta gagatcagac aaacg                                            25

<210> SEQ ID NO 7
<211> LENGTH: 33
<212> TYPE: DNA
<213> ORGANISM: Infectious bursal disease virus

<400> SEQUENCE: 7
tctctagaat gacaaacctg tcagatcaaa ccc                                   33

<210> SEQ ID NO 8
<211> LENGTH: 35
```

```
<212> TYPE: DNA
<213> ORGANISM: Infectious bursal disease virus

<400> SEQUENCE: 8
gggtcgactc acctccttat ggcccggatt atgtc                          35

<210> SEQ ID NO 9
<211> LENGTH: 24
<212> TYPE: DNA
<213> ORGANISM: Cloning vector M13mp18

<400> SEQUENCE: 9
cgccagggtt ttcccagtca cgac                                      24

<210> SEQ ID NO 10
<211> LENGTH: 27
<212> TYPE: DNA
<213> ORGANISM: Cloning vector M13mp18

<400> SEQUENCE: 10
agcggataac aatttcacac aggaaac                                   27

<210> SEQ ID NO 11
<211> LENGTH: 20
<212> TYPE: DNA
<213> ORGANISM: Infectious bursal disease virus

<400> SEQUENCE: 11
ggttgatgtc tgcaacagcc                                           20

<210> SEQ ID NO 12
<211> LENGTH: 20
<212> TYPE: DNA
<213> ORGANISM: Infectious bursal disease virus

<400> SEQUENCE: 12
tcactgctgt cacatgtggc                                           20

<210> SEQ ID NO 13
<211> LENGTH: 20
<212> TYPE: DNA
<213> ORGANISM: Infectious bursal disease virus

<400> SEQUENCE: 13
ggcaccgaca atcttatgcc                                           20

<210> SEQ ID NO 14
<211> LENGTH: 20
<212> TYPE: DNA
<213> ORGANISM: Infectious bursal disease virus

<400> SEQUENCE: 14
gatcgtcact gctaggctcc                                           20

<210> SEQ ID NO 15
<211> LENGTH: 33
<212> TYPE: DNA
<213> ORGANISM: Infectious bursal disease virus

<400> SEQUENCE: 15
tctctagaat gacaaacctg caagatcaaa ccc                            33

<210> SEQ ID NO 16
```

<211> LENGTH: 1374
<212> TYPE: DNA
<213> ORGANISM: Infectious bursal disease virus
<220> FEATURE:
<221> NAME/KEY: CDS
<222> LOCATION: (7)..(1368)
<223> OTHER INFORMATION: product: VP2 of IBDV STC strain

<400> SEQUENCE: 16

```
tctaga atg aca aac ctg caa gat caa acc caa cag att gtt ccg ttc        48
       Met Thr Asn Leu Gln Asp Gln Thr Gln Gln Ile Val Pro Phe
         1               5                  10 ata cgg agc ctt ctg atg cca aca acc gga ccg gcg tcc att ccg gac        96
Ile Arg Ser Leu Leu Met Pro Thr Thr Gly Pro Ala Ser Ile Pro Asp
 15                  20                  25                  30 gac acc ctg gag aag cac act ctc agg tca gag acc tcg acc tac aat       144
Asp Thr Leu Glu Lys His Thr Leu Arg Ser Glu Thr Ser Thr Tyr Asn
                 35                  40                  45 ttg act gtg ggg gac aca ggg tca ggg cta att gtc ttt ttc cct gga       192
Leu Thr Val Gly Asp Thr Gly Ser Gly Leu Ile Val Phe Phe Pro Gly
             50                  55                  60 ttc cct ggc tca att gtg ggt gct cac tac aca ctg cag agc aat ggg       240
Phe Pro Gly Ser Ile Val Gly Ala His Tyr Thr Leu Gln Ser Asn Gly
 65                  70                  75 aac tac aag ttc gat cag atg ctc ctg act gcc cag aac cta ccg gcc       288
Asn Tyr Lys Phe Asp Gln Met Leu Leu Thr Ala Gln Asn Leu Pro Ala
         80                  85                  90 agt tac aac tac tgc agg cta gtg agt cgg agt ctc aca gtg agg tca       336
Ser Tyr Asn Tyr Cys Arg Leu Val Ser Arg Ser Leu Thr Val Arg Ser
 95                 100                 105                 110 agc aca ctc cct ggt ggc gtt tat gca cta aac ggc acc gta aac gcc       384
Ser Thr Leu Pro Gly Gly Val Tyr Ala Leu Asn Gly Thr Val Asn Ala
                115                 120                 125 gtg acc ttc caa gga agc ctg agt gaa ctg aca gat gtt agc tac aat       432
Val Thr Phe Gln Gly Ser Leu Ser Glu Leu Thr Asp Val Ser Tyr Asn
            130                 135                 140 ggg ttg atg tct gca acg gcc aac atc aac gac aaa att ggg aat gtc       480
Gly Leu Met Ser Ala Thr Ala Asn Ile Asn Asp Lys Ile Gly Asn Val
145                 150                 155 cta gta ggg gaa ggg gtc acc gtc ctc agc tta ccc aca tca tat gat       528
Leu Val Gly Glu Gly Val Thr Val Leu Ser Leu Pro Thr Ser Tyr Asp
        160                 165                 170 ctt ggg tat gtg agg ctt ggt gac ccc att cct gct ata ggg ctt gac       576
Leu Gly Tyr Val Arg Leu Gly Asp Pro Ile Pro Ala Ile Gly Leu Asp
175                 180                 185                 190 cca aaa atg gta gcc aca tgt gac agc agt gac agg ccc aga gtc tac       624
Pro Lys Met Val Ala Thr Cys Asp Ser Ser Asp Arg Pro Arg Val Tyr
                195                 200                 205 acc ata act gca gcc gat gat tac caa ttc tca tca cag tac caa cca       672
Thr Ile Thr Ala Ala Asp Asp Tyr Gln Phe Ser Ser Gln Tyr Gln Pro
            210                 215                 220 ggt ggg gta aca atc aca ctg ttc tca gcc aac att gat gct atc aca       720
Gly Gly Val Thr Ile Thr Leu Phe Ser Ala Asn Ile Asp Ala Ile Thr
225                 230                 235 agc ctc agc att ggg gga gag ctc gtg ttc caa aca agc gtc caa ggc       768
Ser Leu Ser Ile Gly Gly Glu Leu Val Phe Gln Thr Ser Val Gln Gly
        240                 245                 250 ctt gta ctg ggc gct acc atc tac ctt ata ggc ttt gat ggg act aca       816
Leu Val Leu Gly Ala Thr Ile Tyr Leu Ile Gly Phe Asp Gly Thr Thr
255                 260                 265                 270 gta atc acc aga gct gtg gcc tca gac aat ggg ctg act gcc ggc acc       864
Val Ile Thr Arg Ala Val Ala Ser Asp Asn Gly Leu Thr Ala Gly Thr
```

-continued

```
Val Ile Thr Arg Ala Val Ala Ser Asp Asn Gly Leu Thr Ala Gly Thr
                275                 280                 285
gac aat ctt atg cca ttc aat ctt gtg att ccg acc aac gag ata acc    912
Asp Asn Leu Met Pro Phe Asn Leu Val Ile Pro Thr Asn Glu Ile Thr
            290                 295                 300 cag cca atc aca tcc atc aaa ctg gag ata gtg acc tcc aaa agt ggc    960
Gln Pro Ile Thr Ser Ile Lys Leu Glu Ile Val Thr Ser Lys Ser Gly
            305                 310                 315 ggt cag gca ggg gac cag atg tca tgg tcg gca agt ggg agc cta gca   1008
Gly Gln Ala Gly Asp Gln Met Ser Trp Ser Ala Ser Gly Ser Leu Ala
        320                 325                 330 gtg aca atc cat ggt ggc aac tat cca ggg gcc ctc cgt ccc gtc aca   1056
Val Thr Ile His Gly Gly Asn Tyr Pro Gly Ala Leu Arg Pro Val Thr
335                 340                 345                 350 cta gta gcc tac gaa aga gtg gca aca gga tcc gtc gtt acg gta gcc   1104
Leu Val Ala Tyr Glu Arg Val Ala Thr Gly Ser Val Val Thr Val Ala
                355                 360                 365 ggg gtg agc aac ttc gag ctg atc cca aat cct gaa cta gca aag aac   1152
Gly Val Ser Asn Phe Glu Leu Ile Pro Asn Pro Glu Leu Ala Lys Asn
            370                 375                 380 ctg gtt aca gaa tac ggc cga ttt gac cca gga gcc atg aac tac aca   1200
Leu Val Thr Glu Tyr Gly Arg Phe Asp Pro Gly Ala Met Asn Tyr Thr
        385                 390                 395 aaa ttg ata ctg agt gag agg gac cgt ctt ggc atc aag acc gtc tgg   1248
Lys Leu Ile Leu Ser Glu Arg Asp Arg Leu Gly Ile Lys Thr Val Trp
    400                 405                 410 cca aca agg gag tac act gac ttt cgt gag tac ttc atg gag gtg gcc   1296
Pro Thr Arg Glu Tyr Thr Asp Phe Arg Glu Tyr Phe Met Glu Val Ala
415                 420                 425                 430 gac ctc aac tct ccc ctg aag att gca gga gca ttt ggc ttc aaa gac   1344
Asp Leu Asn Ser Pro Leu Lys Ile Ala Gly Ala Phe Gly Phe Lys Asp
                435                 440                 445 ata atc cgg gcc ata agg agg tgagtcgac                              1374
Ile Ile Arg Ala Ile Arg Arg
            450

<210> SEQ ID NO 17
<211> LENGTH: 453
<212> TYPE: PRT
<213> ORGANISM: Infectious bursal disease virus

<400> SEQUENCE: 17

Met Thr Asn Leu Gln Asp Gln Thr Gln Ile Val Pro Phe Ile Arg
 1               5                  10                  15

Ser Leu Leu Met Pro Thr Thr Gly Pro Ala Ser Ile Pro Asp Asp Thr
                20                  25                  30
Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
        50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Val Asn Ala Val Thr
        115                 120                 125

Phe Gln Gly Ser Leu Ser Glu Leu Thr Asp Val Ser Tyr Asn Gly Leu
```

```
          130                 135                 140
Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Asp Arg Pro Arg Val Tyr Thr Ile
        195                 200                 205

Thr Ala Ala Asp Asp Tyr Gln Phe Ser Ser Gln Tyr Gln Pro Gly Gly
210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ser Asp Asn Gly Leu Thr Ala Gly Thr Asp Asn
        275                 280                 285

Leu Met Pro Phe Asn Leu Val Ile Pro Thr Asn Glu Ile Thr Gln Pro
290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450
```

<210> SEQ ID NO 18
<211> LENGTH: 39
<212> TYPE: DNA
<213> ORGANISM: Gallus gallus
<220> FEATURE:
<221> NAME/KEY: misc_feature
<222> LOCATION: (1)..(14)
<223> OTHER INFORMATION: Artificial sequence

<400> SEQUENCE: 18
cagtgtcgct gcagctcagt gcatgcacgc tcattgccc                                39

<210> SEQ ID NO 19
<211> LENGTH: 49

```
<212> TYPE: DNA
<213> ORGANISM: Gallus gallus
<220> FEATURE:
<221> NAME/KEY: misc_feature
<222> LOCATION: (1)..(14)
<223> OTHER INFORMATION: Artificial sequence

<400> SEQUENCE: 19
gctctagagt cgacaagctt gggggctgcg gaggaacaga gaagggaag            49

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:A synthetic
      oligonucleotide

<400> SEQUENCE: 20
gatcccctcg aggggggggcc                                          20

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence:A synthetic
      oligonucleotide

<400> SEQUENCE: 21 cccccctcgag gg                                                  12

<210> SEQ ID NO 22
<211> LENGTH: 28
<212> TYPE: DNA
<213> ORGANISM: Simian virus 40
<220> FEATURE:
<221> NAME/KEY: misc_feature
<222> LOCATION: (1)..(8)
<223> OTHER INFORMATION: Artificial sequence

<400> SEQUENCE: 22 gcgggccta attgtttgtg tattttag                                   28

<210> SEQ ID NO 23
<211> LENGTH: 29
<212> TYPE: DNA
<213> ORGANISM: Simian virus 40
<220> FEATURE:
<221> NAME/KEY: misc_feature
<222> LOCATION: (1)..(8)
<223> OTHER INFORMATION: Artificial sequence

<400> SEQUENCE: 23
ttggtaccgc ttacaattta cgcgttaag                                 29

<210> SEQ ID NO 24
<211> LENGTH: 24
<212> TYPE: DNA
<213> ORGANISM: Infectious bursal disease virus

<400> SEQUENCE: 24
caccgtcctc agcttaccca catc                                      24

<210> SEQ ID NO 25
<211> LENGTH: 23
<212> TYPE: DNA
```

```
<213> ORGANISM: Infectious bursal disease virus

<400> SEQUENCE: 25
acgacggatc ctgttgccac tct                                            23

<210> SEQ ID NO 26
<211> LENGTH: 24
<212> TYPE: DNA
<213> ORGANISM: Gallid herpesvirus 2

<400> SEQUENCE: 26
ggggaagtct tccggttaag ggac                                           24

<210> SEQ ID NO 27
<211> LENGTH: 24
<212> TYPE: DNA
<213> ORGANISM: Gallid herpesvirus 2

<400> SEQUENCE: 27
ggtgcaattc gtaagaccga tggg                                           24
```

AVIAN HERPESVIRUS-BASED RECOMBINANT INFECTIOUS BURSAL DISEASE VACCINE

BACKGROUND OF THE INVENTION

1. Field of the Invention

Figure 1:
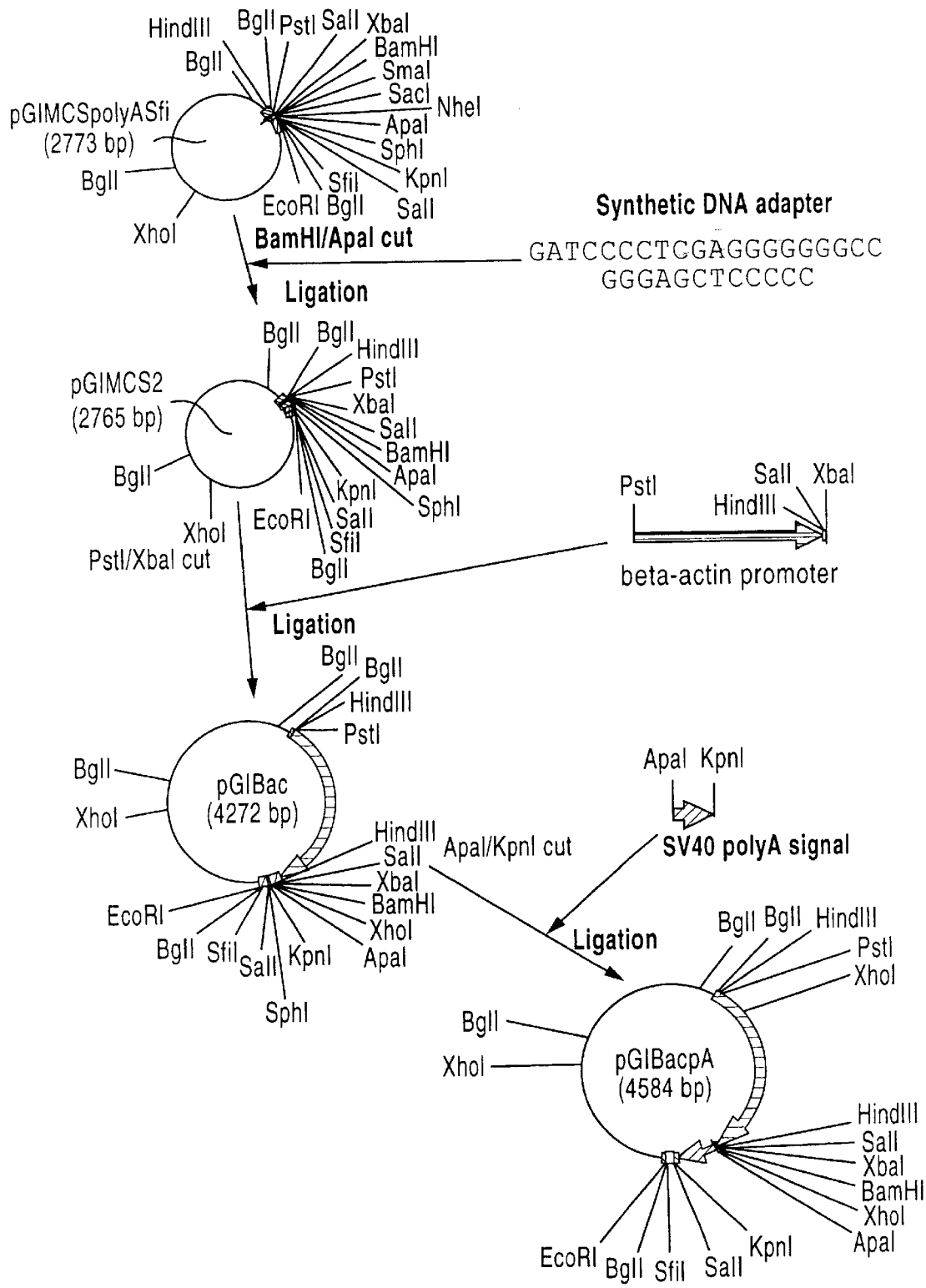

The present invention provides an avian recombinant herpesvirus comprising cDNA of VP2 (VP2 cDNA) of the IBDV Delaware Variant E strain, a member of IBDV variant strain subtype.

2. Related Art

Infectious Bursal Disease, often referred to as Gumboro disease, is caused by the highly transmissive Infectious Bursal Disease Virus (IBDV) and inflicts a great economic loss on the poultry industry. There are two serotypes of IBDV: serotype 1 and 2. Serotype 1 is pathogenic for chickens. Many IBDV strains are classified as serotype 1. Based on pathogenicity and antigenicity, serotype 1 strains are further divided into four subtypes: classical virulent, attenuated, variant, and very virulent strains (Y. C. Cao et al., 1998, *Avian Diseases*, 42: 340–351). For instance, STC, 52/70, 002–73, etc., are classified as classical virulent strains. Bursine, Bursa-Vac-3, Bursa-Vac-M, CU-1, PBG98, etc., are classified as attenuated strains. Delaware E, A, GLS, GZ902, Ark, AL-2, etc., are classified as variant strains, and OKYM, UK661, F9502, HK46, etc., are classified as very virulent strains.

The IBDV genome consists of two double-stranded RNA segments: Segment A and B. Segment A encodes a 115 kd precursor polyprotein, which is processed auto-catalytically by VP4 to give VP2, VP3 and VP4. Segment A also encodes VP5 that is translated in a different reading-frame from VP2 to VP4. Reportedly, VP5 is related to the virulence of the virus but its detailed function remains to be elucidated. Earlier studies using anti-IBDV monoclonal antibodies indicate that VP3 has one serotype-specific epitope and another non-overlapping epitope, but VP3 does not contain a major virus-neutralizing epitope. On the contrary, VP2 has independent epitopes that elicit IBDV neutralizing antibodies (U.S. Pat. Nos. 5,350,575, 5,849,575). The amino acid sequence of VP2 differs from strain to strain (H. G. Heine et al., 1991, *J. Gen. Virol.* 72: 1835–1843, T. V. Dormitorio et al., 1997, *Avian Diseases* 41:36–44, and Y. C. Cao, et al., 1998, *Avian Diseases* 42: 340–351), and antigenic differences among IBDV subtypes are likely due to these sequence variances.

In the United States, Infectious Bursal Disease has been controlled by passive immunity passed from the hen to the chick. In short, high antibody levels are elicited using killed IBDV vaccines so that chicks acquire high maternal antibody levels. These high maternal antibody levels protect the chick through the first few weeks of life. Problems associated with this strategy are that all chicks do not acquire the same level of maternal antibody. On a flock basis it is hard to predict when maternal antibodies wane and as a result some chicks are unprotected. In the United States in the 1980s, variant IBD viruses breaking through passive immunity elicited with classic vaccine strains caused disease in the United States (H. G. Heine et al., 1991, *J. Gen. Virol.* 72:1835–1843). The most prominent variant virus at this time was Delaware Variant E. Variant IBDV viruses were and are still being added to killed vaccines for protection against variant strains. In Europe, many cases of Infectious Bursal Disease were reported among chickens that had high titers of IBDV maternal antibody. These chickens were killed by the natural infection of a very virulent strain even though hens were administered IBD vaccines (M. D. Brown et al., 1994, *J. Gen. Virol.* 75:675–680). These incidents indicate that antigenic differences between vaccine and prevalent disease-causing strains should be seriously considered. Development of a vaccine that protects chickens from a variety of different subtypes of IBDV is desirable for the poultry industry.

Construction of a recombinant avian herpesvirus harboring a protective antigen gene from other avian pathogens as well as its use as a poultry vaccine is suggested in U.S. Pat. Nos. 5,834,305, 5,853,733, 5,928,648, 5,961,982, WO 87/04463 and WO 99/18215 etc. VP2 is a protective antigen of IBDV and Segment A of IBDV includes VP2 gene. The recombinant avian herpesvirus comprised of the VP2 gene or Segment A and its use as an IBD vaccine is reported in U.S. Pat. No. 5,733,554, WO 89/01040, WO 93/25665, WO 96/05291 or WO99/18215. R. Darteil et al., and K. Tsukamoto et al. also reported similar recombinant avian herpesvirus-vectored IBD vaccines (R. Darteil et al., 1995, *Virology*, 211:481–490, K. Tsukamoto et al., 1999, *Virology*, 257:352–362). In WO 89/01040, under the control of the pseudorabies virus gpX promoter, cDNA of Segment A including VP2, VP3 and VP4 genes was inserted into the BamHI #16 fragment in the UL43 gene of herpesvirus of turkeys (HVT) to generate a recombinant herpesvirus, S-HVT-003. Segment A was derived from the IBDV S4047 strain but its subtype is not divulged in the specification. In addition, R. Darteil et al. (R. Darteil et al., 1995, *Virology*, 211:481–490, U.S. Pat. No. 5,733,554) reported a few recombinant HVTs harboring VP2 gene from the IBDV 52/70 strain, a member of the classical virulent strain subtype. For instance, vHVT1 comprises the said VP2 gene in the RR2 (UL40) region, which is driven by the RR2 intrinsic promoter. vHVT2 comprises the VP2 gene under the control of the exogenous CMV-IE promoter in the gI (US7) region. vHVT4 comprises the VP2 gene driven by the same promoter in the UL43 region. Although the UL40 and US7 regions seemed not to be essential for in vitro virus growth, vHVT1 and vHVT2 did not grow well in vivo. On the contrary, vHVT4 conferred good protection in SPF chickens against challenge with the IBDV 52/70 strain. However, in this experiment, the challenge conditions seem to have been mild since the group of positive control chickens, vaccinated with an inactivated IBDV vaccine, was also completely protected. Inactivated vaccines do not induce protective immunity against very virulent strains or European types of virulent strains.

In addition, WO 99/18215 describes a recombinant HVT, HF003, which has the VP2 gene inserted into the inter-ORF region between UL45 and UL46. The said VP2 gene was from IBDV OKYM, a member of the very virulent strain subtype, which was isolated in Japan. However, HF003 was proven to confer protection only against the IBDV OKYM strain.

In consequence, several avian recombinant herpesviruses comprising IBDV genes have been reported so far, but none of these induced in chickens protective immunity against a variety of different subtypes of IBDV. In other words, no knowledge is available as to which VP2 gene is suitable for the construction of the recombinant avian herpesvirus that will give protection against the broad range of IBDV subtypes.

SUMMARY OF THE INVENTION

The present invention provides an avian recombinant herpes virus modified by the presence of the cDNA encoding the VP2 gene of the Delaware Variant E strain of IBDV. In chickens, the recombinant virus elicited excellent protective immunity against a variety of different IBDV strains belonging to two subtypes of serotype 1.

More specifically, the present invention provides an avian recombinant herpesvirus modified by the insertion of cDNA of the VP2 gene that is derived from Delaware Variant E, a member of the IBDV variant strain subtype. The insertion site of the VP2 cDNA is in a region non-essential for the avian herpesvirus growth (the non-essential region). The present invention further provides an Infectious Bursal Disease vaccine including the said avian recombinant herpesvirus as an active ingredient.

The present invention is described below in more details.

VP2 cDNA

As well as being derived from the Delaware Variant E strain, any VP2 cDNA can be used for the purpose of the present invention.

The amino acid sequence of VP2 differs from strain to strain (T. V. Dormitorio et al., 1997, *Avian Diseases* 41:36–44, Y. C. Cao, et al., 1998, *Avian Diseases* 42: 340–351.), suggesting that even among variant strains, the nucleotide sequence of VP2 cDNA may differ.

The nucleotide sequence of the VP2 cDNA of the Delaware Variant E strain is reported in the literature (H. G. Heine et al., 1991, *J. Gen. Virol.* 72: 1835–1843, European Molecular Biology Laboratory (EMBL) database (Accession# AF133904)). In addition, the sequence shown in SEQ ID No.1 is also representing VP2 cDNA because the VP2 gene sequence slightly differs from clone to clone. VP2 cDNA shown in SEQ ID NO.1 is, therefore, only an example that is suitable for the purpose of the present invention.

VP2 cDNA derived from the virus genome can be used with or without modifications to generate the avian recombinant herpesvirus. For instance as shown in SEQ ID NO.1, the VP2 cDNA can be modified to have a stop signal following the 453rd amino acid codon and restriction sites at both N- and C-terminals to facilitate its subcloning into the plasmid vector.

Promoter

As long as being functional in the avian herpesvirus-infected cells, any promoter can be used to express the inserted VP2 gene in the present invention. For instances, the exogenous promoter such as Cytomegalovirus (CMV) promoter, Rouse Sarcoma virus (RSV) promoter, SV40 early promoter, endogenous promoter such as MDV-1 gB promoter (U.S. Pat. No. 6,013,261) and the chicken beta-actin promoter are suitable. Among these, the chicken beta-action promoter is most favorable because it facilitates the high expression of the VP2 gene.

The nucleotide sequence of the chicken beta-action promoter is reported in the literature (T. A. Kost et al., 1983, *Nucleic Acids Res.* 11:8287–8301). However, the promoter for the present invention need not necessarily be identical to that reported. In fact, as shown in SEQ ID NO. 3, the beta-actin promoter cloned from chicken cells by the inventors had a slightly different sequence from that reported.

Addition of Other Nucleotides to VP2 cDNA

To stabilize the transcribed mRNA, the polyA signal can be added at 3' terminus of the VP2 gene. Any polyA signal that enhances Eukaryotic gene expression is appropriate. An example is the SV40 polyA signal, which is included in pBK-RSV (STRATAGENE, Cat #212210).

Avian Herpesvirus

Any of serotype 1, serotype 2 or serotype 3 Marek's disease virus can be used as a backbone avian herpesvirus. However, taking their use as the poultry vaccine into consideration, Marek's disease vaccine strains such as HVT FC126 (serotype 3), SB1 (serotype 2) or Rispens (serotype 1) are suitable for the purpose of the present invention.

Non-essential Regions for the Gene Insertion

There are many reports of the non-essential regions of the avian herpesvirus, a non-essential region being dispensable for the virus growth and suitable for foreign gene insertion. VP2 cDNA can be inserted into any of these regions. For instance, the UL43 gene described in WO 89/01040, the US2 in WO 93/25665 and the inter-ORF region between UL44 and UL46 in WO 99/18215 can be used for the VP2 cDNA insertion. Among these, the inter-ORF region between UL44 and UL46 is most suitable in regard of the virus stability.

For the present invention, the non-essential region can newly be identified by the following general procedures. First, the avian herpesvirus DNA fragments of the appropriate length are cloned into an *E. coli* plasmid and physically mapped by restriction enzyme analysis. Then, a gene cassette consisting of a promoter and a marker gene is inserted into an appropriate restriction site of the cloned DNA fragment. As described later, if the homologous recombination with the resultant homology vector resulted in a recombinant virus expressing the inserted marker gene and if it is stable in vitro and in vivo, the originally selected DNA fragment should be a non-essential region suitable for VP2 cDNA insertion. To check the stability, the genome DNA of recombinant viruses was propagated on the marrow of purification, and after five more passages in vitro and in vivo was prepared and subjected to Southern hydridization analysis. If the result of the analysis indicates that the genome structures before and after passaging are identical, the recombinant virus is stable.

Construction of the Avian Recombinant Herpesvirus

For the present invention, any known method of generating the recombinant avian herpesvirus is applicable. A typical example is as follows. (1) First, as described above, a recombinant plasmid is constructed, which includes a non-essential region of the avian herpesvirus. Then, preferably with a promoter at the 5' terminus and a polyA signal at the 3' terminus, VP2 cDNA is inserted into the said non-essential region to generate a homology vector. (2) The resultant vector is transfected into chicken embryo fibroblast (CEF) cells infected with parent avian herpesvirus or co-transfected into CEF cells with infectious avian herpesvirus genomic DNA. Transfection is performed by any known method. (3) The transfected CEF cells are inoculated into culture plates and incubated till the virus plaques become visible. (4) The identifiable plaques include recombinant viruses as well as parent wild-type viruses. The recombinant virus is purified from these plaques by any known method. For instance, CEF cells having plaques are diluted to an appropriate concentration, transferred to the 96-well plates and recombinant plaques are selected by antigen-antibody reaction using the monoclonal antibody against the IBDV VP2 as the primary antibody.

Infectious Bursal Disease Vaccine

The recombinant avian herpesvirus in the present invention is used as a chicken Infectious Bursal Disease vaccine since it includes the VP2 gene. VP2 is a protective antigen of IBDV. a causative virus of Infectious Bursal Disease. In addition, when Marek's disease virus (serotype 1, serotype 2 or serotype 3 MDV) is used as a backbone virus for VP2 gene insertion, it can be a polyvalent vaccine against both Infectious Bursal and Marek's diseases.

For the purpose of the present invention, the poultry vaccine consisting mainly of the recombinant avian herpesvirus may include chicken cells and/or ingredients of culture media in addition to the serotype 1, serotype 2 or serotype 3 recombinant MDV. The vaccine may contain other ingredients such as preservatives, so long as these are not pharmacologically detrimental.

The poultry vaccine of the present invention may be combined with any recombinant or non-recombinant viruses. For example, serotype 1 or serotype 2 MDV vaccine strain can be mixed with the vaccine consisting mainly of the serotype 3 recombinant MDV.

Any known method is applicable to the preparation of the poultry recombinant polyvalent vaccine of the present invention. For instance, the recombinant MDV of the present invention is inoculated into permissive culture cells such as CEF cells and grown to an appropriate titer. Then, the cells are scraped off from culture plates or bottles by scraper or by trypsin treatment and subjected to centrifugation. Cells separated from the supernatant are then suspended in culture medium containing 10% dimethyl sulfoxide and stored in liquid nitrogen.

The avian polyvalent vaccine is administered to chickens by any known method of inoculating the Marek's disease vaccine. For instance, the vaccine of the present invention is suspended in the phosphate buffer saline to give $10–10^5$, or more favorably $10^{2–10^4}$ PFU/dose, and inoculated into napes of one day of age chickens subcutaneously or into embryonated eggs by syringe or by any apparatus for injection.

The avian polyvalent vaccine gives chickens at least 50% protection against the challenge with a variety of different subtypes of IBDV. Different subtypes mean the combination of two or more subtypes of IBDV selected from at least two, or more favorably from three, or more favorably from all subtypes of IBDV. The combination of three strains, STC belonging to the classical virulent subtype, Delaware E and AL-2 belonging to the variant subtype, is an example.

In the present invention, the protection against the IBDV challenge is determined by the ratio of protected birds to total tested birds. Essentially, the vaccinated chickens are challenged intraocularly with $10^3$ $EID_{50}$/dose or more of IBDV and necropsied one week later to detect any notable lesions. Protected birds without notable lesions have (1) the weight ratio of the bursa of Fabricius to the body (B/B ratio) which is not statistically different from that of non-vaccinated, non-challenged chickens, and show (2) no malformation of the Bursa of Fabricius such as edematization, hemorrhage, yellowish exudate, discoloration, atrophy, or gelatinous exudate. The challenge testing is valid only when all chickens of the non-vaccinated and challenged control show the notable legions indicating 0% protection.

BRIEF DESCRIPTION OF THE DRAWING FIGURES

FIG. 1 Construction of the plasmid pGIBacpA

Figure 2:
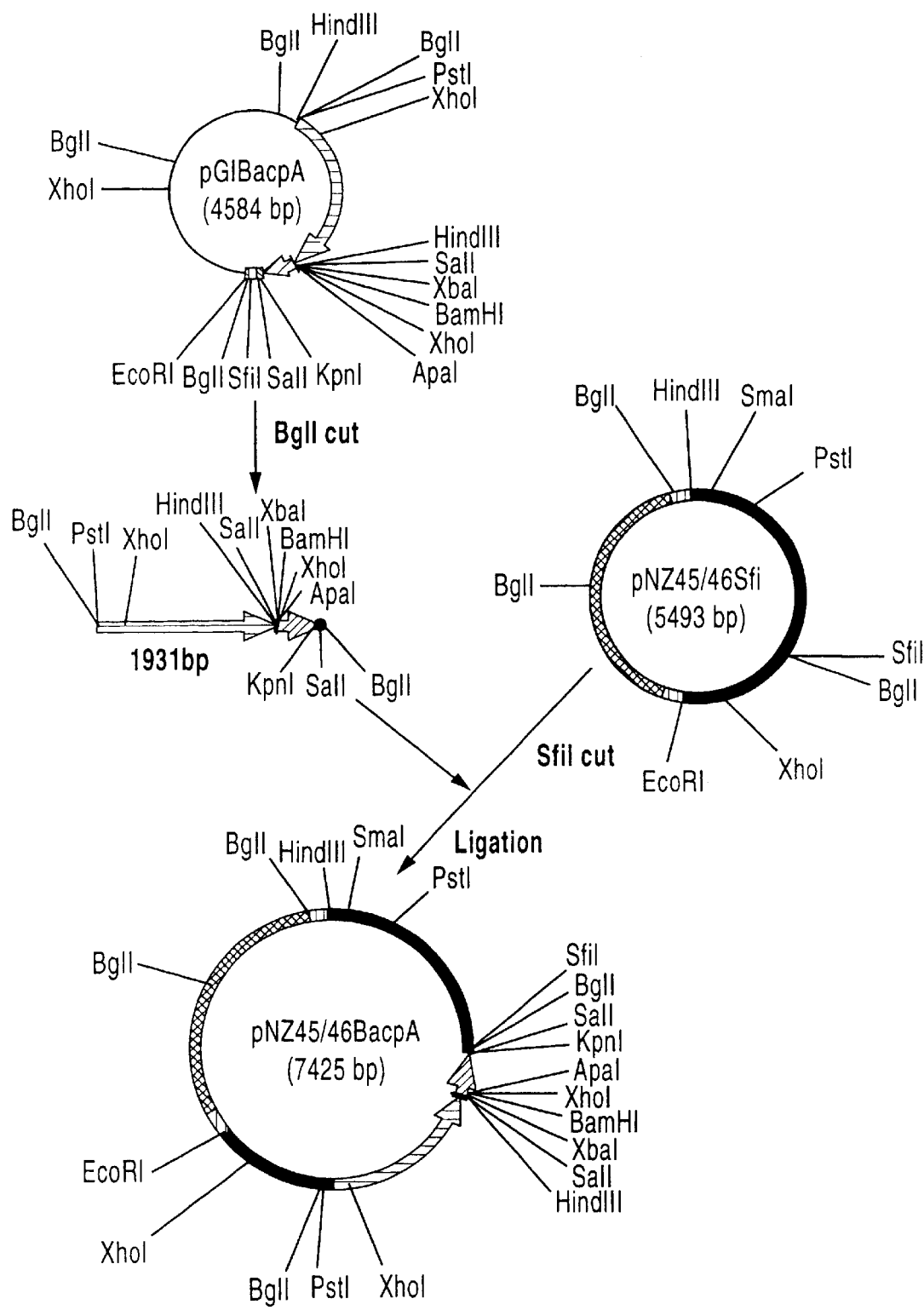

FIG. 2 Construction of the plasmid pNZ45/46BacpA

Figure 3:
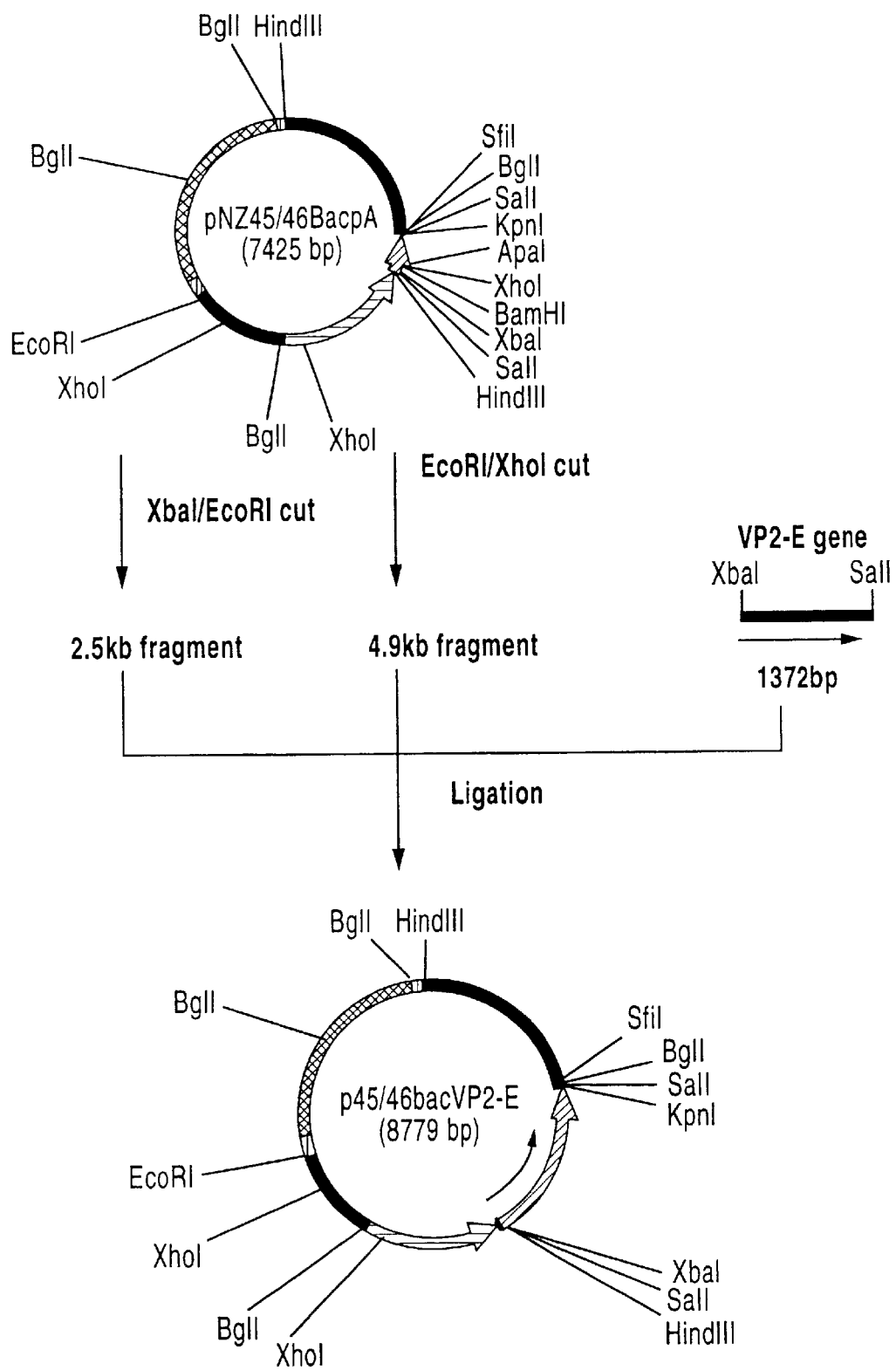

FIG. 3 Construction of the plasmid p45/46bacVP2-E

Figure 4:
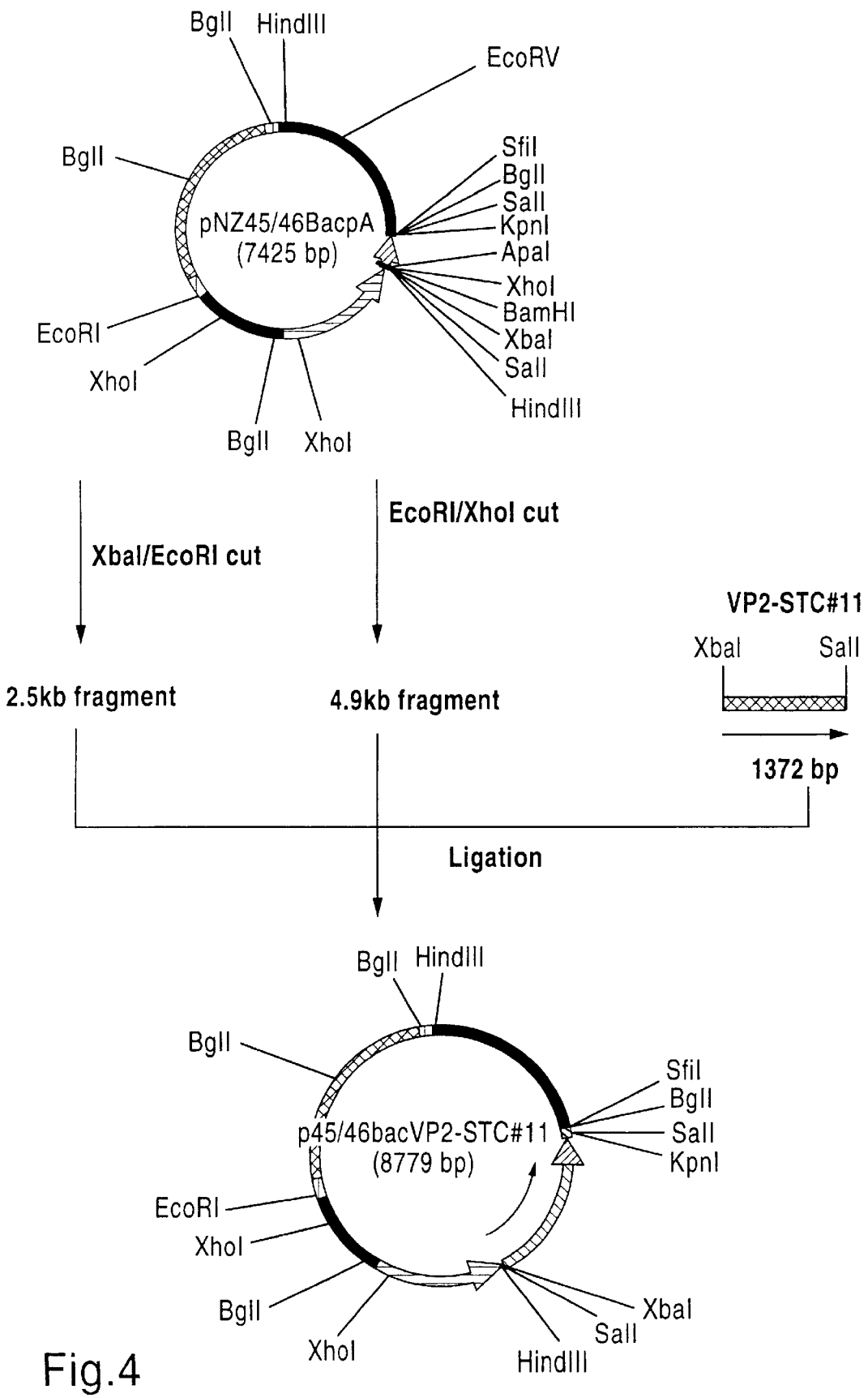

FIG. 4 Construction of the plasmid p45/46bacVP2-STC#11

Figure 5:
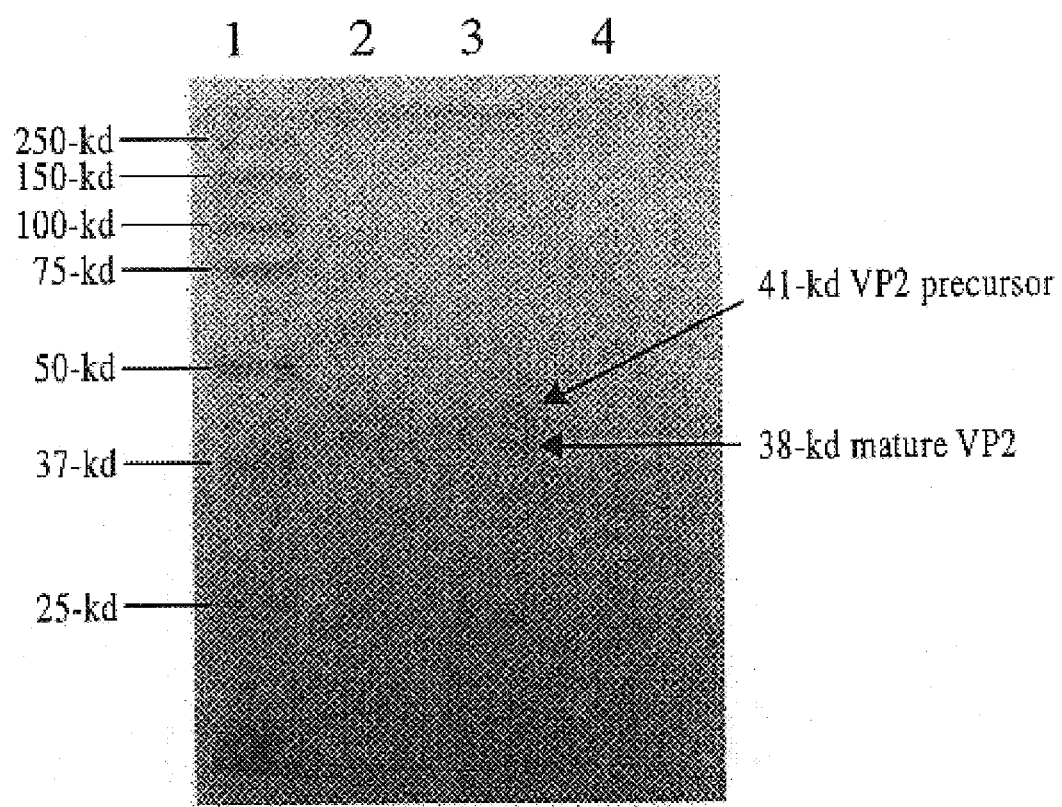

FIG. 5 SDS-PAGE of VP2 expressed by rHVT/IBD-E

LIST OF THE SEQ ID SEQUENCES

SEQ ID NO. 1: Sequence of the VP2 gene derived from IBDV Delaware Variant E strain SEQ ID NO. 2: Amino acid sequence of Delaware Variant E VP2

SEQ ID NO. 3: Sequence of the chick beta-actin promoter gene

SEQ ID NO. 4: Primer VP2-3R

SEQ ID NO. 5: Primer VP2-3-1

SEQ ID NO. 6: Primer VP2-5-1

SEQ ID NO. 7: Primer VP2-5-2E

SEQ ID NO. 8: Primer VP2-3-2

SEQ ID NO. 9: M13 Primer P7

SEQ ID NO. 10: M13 Primer P8

SEQ ID NO. 11: Primer 432S

SEQ ID NO. 12: Primer 608AS

SEQ ID NO. 13: Primer 798S

SEQ ID NO. 14: Primer 1018AS

SEQ ID NO. 15: Primer VP2-5-2S

SEQ ID NO. 16: Sequence of the VP2 gene derived from IBDV STC strain

SEQ ID NO. 17: Amino acid sequence of STC VP2

SEQ ID NO.18: Primer PrBac1

SEQ ID NO. 19: Primer PrBac2

SEQ ID NO. 20: Oligonucleotide Ad-B-A-U

SEQ ID NO. 21: Oligonucleotide Ad-B-A-L

SEQ ID NO. 22: Primer PolyA-F

SEQ ID NO. 23: Primer PolyA-R

SEQ ID NO. 24: Primer VP2-F

SEQ ID NO. 25: Primer VP2-R

SEQ ID NO. 26: Primer 45/46-F

SEQ ID NO. 27: Primer 45/46-R

DETAILED DESCRIPTION OF THE INVENTION

The plasmid construction was essentially performed by the standard molecular biology techniques (Molecular Cloning: A Laboratory Manual. 2nd Edition, Cold Spring Harbor Laboratory, Cold Spring Harbor, N.Y. 1989). DNA restriction fragments were electrophoresed on agarose gels and purified with QIAquick Gel Extraction Kit™ (QIAGEN, Cat #28704).

Herpesvirus of turkeys FC126 strain (Witter R. L. et al. *Am. J. Vet. Res.* 1970, 31, 525–538) was used as a backbone virus to generate the avian recombinant herpesvirus.

EXAMPLE 1

Preparation of VP2 cDNA from IBDV Delaware Variant E and STC Strains 1.1. Preparation of VP2 cDNA from IBDV Delaware Variant E Strain The Delaware Variant E strain, a serotype 1 IBDV (a gift from Biomune Company, Lenexa, Kans.) was inoculated into chickens. One week later, lysates of Bursa of Fabricius were prepared, which contained $10^{5.32}$ $EID_{50}$/ml of IBDV. From these lysates, total viral RNA was isolated with Catrimox-14™ RNA Isolation Kit Ver.2.11 (TaKaRa, Japan, Cat # WA005) under the conditions recommended by the supplier. The extracted total RNA was then subjected to RT-PCR using BcaBEST™ RNA PCR kit Ver.1.1 (TaKaRa, Japan, Cat. #RR023A). In the RT-PCR operation, VP2-3R primer (SEQ ID NO. 4) and BcaBEST polymerase were used for reverse transcription, and primers VP2-3-1 (SEQ ID NO. 5), VP2-5-1 (SEQ ID NO. 6) and Bca-Optimized Taq polymerase for cDNA synthesis.

```
VP2-3R
5'-CTACACCTTCCCCAATTGCATGGGC-3'        (SEQ ID NO.4)

VP2-3-1
5'-GGTGGGAACAATGTAGAGACCACCGG-3'       (SEQ ID NO.5)

VP2-5-1
5'-ATGGTTAGTAGAGATCAGACAAACG-3'        (SEQ ID NO.6)
```

Using the obtained cDNA as a template, a 1.4 kb DNA fragment was amplified by nested PCR. Primers VP2-5-2E (SEQ ID NO. 7), VP2-3-2 (SEQ ID NO. 8) and TaKaRa Taq™ (TaKaRa, Japan, Cat. #R001A) or Pfu DNA polymerase (STRATAGENE, Cat. #600153) were used for the nested PCR. In the operation, annealing of DNA was performed at 55° C. and PCR was repeated for 30 cycles.

```
VP2-5-2E
5'-TCTCTAGAATGACAAACCTGTCAGATCAAACCC     (SEQ ID NO.7)
                                    -3'

VP2-3-2
5'-GGGTCGACTCACCTCCTTATGGCCCGGATTATGT    (SEQ ID NO.8)
                                    C-3'
```

The amplified 1.4 kb cDNA was purified with QIAquick PCR purification Kit (QIAGEN, Cat. #28104), ligated either to pCR2.1-TOPO vector (INVITROGEN, Cat. #K4500-01) or to the SmaI site of the alkaline phosphatase-treated pUC18 and used for *E. coli* transformation.

Then, from ampicillin-resistant transformants, five independent plasmid clones (clone #1 to 5) were extracted and subjected to DNA sequencing. Sequencing of the inserted VP2 was performed on DNA sequencer CEQ2000 (BECKMAN COULTER) by the dye-terminator method using DTCS Kit (BECKMAN COULTER, Cat. #P/N 608000) and with eight sequencing primers (SEQ ID NO. 7 to 14).

```
VP2-5-2E
5'-TCTCTAGAATGACAAACCTGTCAGATCAAACCC (SEQ ID NO.7)
                                    -3'

VP2-3-2
5'-GGGTGGACTCACCTCCTTATGGCCCGGATTATG (SEQ ID NO.8)
                                  TC-3'

M13 Primer P7
5'-CGCCAGGGTTTTCCCAGTCACGAC-3'         (SEQ ID NO.9)

M13 Primer P8
5'-AGCGGATAACAATTTCACACAGGAAAC-3'      (SEQ ID NO.10)

432S
5'-GGTTGATGTCTGCAACAGCC-3'             (SEQ ID NO.11)

608AS
5'-TCACTGCTGTCACATGTGGC-3'             (SEQ ID NO.12)

798S
5'-GGCACCGACAATCTTATGCC-3'             (SEQ ID NO.13)

1018AS
5'-GATCGTCACTGCTAGGCTCC-3'             (SEQ ID NO.14)
```

Although a few base substitutions were observed as shown in Table 1, each of five VP2 cDNA was confirmed to be that from the IBDV Delaware variant E strain. Deduced amino acid sequences of five clones are summarized in Table 2.

As indicated in Table 2, the deduced amino acid sequence of clone #5 (VP2-E #5) was identical to that reported as Delaware Variant E VP2 (J. Gen. Virol. 1991, 72, 1835–1843). This clone was named VP2-E and used for further experiments. The nucleotide and deduced amino acid sequences of VP2-E (XbaI site upstream from 5' terminus to SalI site at 3'-terminus) were shown in SEQ ID NO. 1 and 2.

TABLE 1

Pair distances of DNA sequences
Percent Similarity (%)

|         | IBDV E | VP2-E#1 | VP2-E#2 | VP2-E#3 | VP2-E#4 | VP2-E#5 |
|---------|--------|---------|---------|---------|---------|---------|
| IBDV E  |        | 99.5    | 99.3    | 99.2    | 99.4    | 99.7    |
| VP2-E#1 |        |         | 99.4    | 99.3    | 99.5    | 99.8    |
| VP2-E#2 |        |         |         | 99.3    | 99.5    | 99.6    |
| VP2-E#3 |        |         |         |         | 99.3    | 99.6    |
| VP2-E#4 |        |         |         |         |         | 99.7    |
| VP2-E#5 |        |         |         |         |         |         |

IBDV E is a sequence of VP2 from IBDV Delaware Variant E published in J Gen. Virol. (1991), 72, 1835–43. Each of VP2-E#1 to #5 is a DNA sequence of VP2 cDNA cloned in this study.

TABLE 2

Pair distances of deduced amino acid sequences
Percent Similarity (%)

|         | IBDV-E | VP2-E#1 | VP2-E#2 | VP2-E#3 | VP2-E#4 | VP2-E#5 |
|---------|--------|---------|---------|---------|---------|---------|
| IBDV-E  |        | 99.3    | 99.1    | 99.1    | 99.6    | 100.0   |
| VP2-E#1 |        |         | 99.2    | 98.5    | 98.7    | 99.1    |
| VP2-E#2 |        |         |         | 98.2    | 98.5    | 98.9    |
| VP2-E#3 |        |         |         |         | 98.7    | 99.1    |
| VP2-E#4 |        |         |         |         |         | 99.3    |
| VP2-E#5 |        |         |         |         |         |         |

1.2. Preparation of VP2 cDNA from IBDV STC Strain

The STC strain, a serotype 1 IBDV, belongs to the classical subtype and has been used as the standard IBDV challenge virus in the US. VP2 cDNA was prepared from $10^4$ $EID_{50}$ of STC essentially as described in EXAMPLE 1.1 using VP2-5-2S (SEQ ID NO. 15) as a primer. The sequencing of four independent clones (#1, 9, 11, and 17) was carried out similarly with primer VP2-5-2S instead of VP2-5-2E. When compared with the sequence reported in literature (*J. Gen. Virol.* 71: 569–577, 1990), clones #1 and #9 had one base deletion and clones #11 and #17 had 26 and 29 substitutions, respectively.

The deduced amino acid sequence of clone #11 differed from that reported as STC VP2 by 6 and clone #17 by 8 amino acids. Therefore, clone #11 was named VP2-STC#11 and used for further experiments. The nucleotide and deduced amino acid sequences of VP2-STC#11 (XbaI site upstream from 5' terminus to SalI site at 3'-terminus) were shown in SEQ ID NO. 16 and 17.

VP2-5-2S (SEQ ID NO. 15)
5'-TCTCTAGAATGACAAACCTGCAAGATCAAACCC-3'

EXAMPLE 2

Isolation of the Chick Beta-Actin Promoter Gene

Using cellular DNA of CEF cells as a template, amplified 1.5 kb DNA containing the chicken beta-actin promoter was obtained by PCR. PrBac1 (SEQ ID NO. 18) and PrBac2 (SEQ ID NO. 19) were the primer set used for PCR. The obtained DNA was digested with PstI and XbaI and inserted into pUC18. The sequence of the inserted DNA was determined as described before and confirmed to be that of the beta-actin promoter which was 1,525 bp long (SEQ ID NO. 3).

```
PrBac1
5'-CAGTGTCGCTGCAGCTCAGTGCATGCACGCTCA   (SEQ ID NO.18)
TTGCCC-3'

PrBac2
5'-GCTCTAGAGTCGACAAGCTTGGGGGCTGCGGAG   (SEQ ID NO.19)
GAACAGAGAAGGGAAG-3'
```

EXAMPLE 3

Construction of Homology Vectors 3.1. Construction of Plasmid pGIBacpA

A DNA adapter consisting of synthetic oligonucleotides Ad-B-A-U (SEQ ID NO. 20) and Ad-B-A-L (SEQ ID NO. 21) was inserted between BamHI and ApaI sites of pGIMCSpolyASfi (2,773 bp, WO 99/18215) to generate plasmid pGIMCS2 (2,765 bp).

```
DNA adapter 5'-GATCCCCTCGAGGGGGGCC-3'
                3'-GGGAGCTCCCCC-5'
```

Plasmid pGIMCS2 was then digested with PstI and XbaI and ligated with the beta-actin promoter described in EXAMPLE 2 to give plasmid pGIBac (4,272 bp).

Next, using pBK-CMV (STRATAGENE, Cat. #212209) as a template and PolyA-F (SEQ ID NO. 22) and PolyA-R (SEQ ID NO. 23) as a set of primers, DNA including SV40 polyA signal was amplified by PCR. Digestion of the amplified DNA with ApaI and KpnI gave a 334 bp SV40 polyA signal DNA. The DNA was then inserted into pGIBac, which had been digested with ApaI and KpnI, to generate pGIBacpA (4,584 bp, FIG. 1).

```
PolyA-F
5'-GCGGGCCCTAATTGTTTGTGTATTTTAG-3'   (SEQ ID NO.22)

PolyA-R
5'-TTGGTACCGCTTACAATTTACGCGTTAAG-3'  (SEQ ID NO.23)
```

3.2. Construction of plasmid pNZ45/46BacpA

Plasmid pGIBacpA was digested with BglI, electrophoresed on agarose gels and 1,931 bp DNA fragment was recovered from the gels. The recovered fragment was then ligated to plasmid pNZ45/46Sfi (5,493 bp, WO 99/18215), which had previously been digested with SfiI, to obtain pNZ45/46BacpA (7,425 bp, FIG. 2).

3.3. Construction of Plasmid p45/46bacVP2-E

VP2-E cDNA described in EXAMPLE 1.1 was digested with XbaI and SalI. The resultant 1,372 bp fragment of VP2-E was ligated with 2.5-kbp XbaI-EcoRI and 4.9-kbp EcoRI-XhoI fragments, both of which were excised from pNZ45/46BacpA, to generate p45/46bacVP2-E (8,779 bp, FIG. 3).

3.4. Construction of Plasmid p45/46bacVP2-STC#11

VP2-STC#11 DNA described in EXAMPLE 1.2 was digested with XbaI and SalI to give 1,372 bp VP2-STC#11 DNA. This DNA was then ligated with 2.5-kb XbaI-EcoRI and 4.9-kbp EcoRI-XhoI fragments from pNZ45/46BacpA, to generate p45/46bacVP2-STC#11 (8,779 bp, FIG. 4).

EXAMPLE 4

Isolation and Purification of Recombinant HVT 4.1. Isolation of rHVT/IBD-E

Viral DNA of HVT FC126 strain (wt-HVT) was prepared as described by Morgan et al. (*Avian Diseases*, (1990) 34:345–351).

$10^7$ primary CEF cells were suspended in Saline G (0.14 M NaCl, 0.5 mM KCl, 1.1 mM $Na_2HPO_4$, 1.5 mM $NaH_2PO_4$, 0.5 mM $MgCl_2$, 0.011% glucose) and co-transfected with 5 μg of p45/46bacVP2-E and 25 μg of viral DNA by electroporation. Electroporation was performed on Bio-Rad Gene Pulser. Transfected cells were incubated for 10 min at room temperature and transferred to one well of a 6-well plate, which contained 5 ml medium consisting of Leibovitz's L-15, McCoy's 5A Medium (1:1) and 4% calf serum (LM (+) medium). After incubating at 37° C. for 6 days in 5% $CO_2$, harvested cells were diluted serially in freshly prepared secondary CEF cells, plated to the 96-well plates, and incubated for three more days.

When the plaques became visible, the cells were detached from plates by trypsinization, diluted in freshly prepared secondary CEF cells, transferred equally to two 96-well plates and incubated for 3 days to visualize the plaques. One of two plates was then stained with anti-VP2 monoclonal antibody R63 (ATCC #: HB-9490) as the primary antibody. After detecting the well containing the stained recombinant plaques, cells from the corresponding well of the other plate were recovered, diluted in fresh secondary CEF cells and transferred equally to two 96-well plates to complete the first round of purification.

The purification procedure was repeated until every obtained plaque was stained positively by monoclonal antibody R63. The purified recombinant HVT was designated rHVT/IBD-E.

4.2. Isolation of rHVT/IBD-STC#11

Using p45/46bacVP2-STC#11 instead of p45/46bacVP2-E, the purified rHVT/IBD-STC#11 was constructed by the same method described in EXAMPLE 4.1.

EXAMPLE 5

Verification of the Genomic Structure and Stability of the Recombinant Virus 5.1. Southern Hybridization The purified rHVT/IBD-E was propagated on CEF cells of two 150-mm dishes to obtain the confluent plaques. Cells were recovered from dishes by scraping, transferred to Falcon tubes and subjected to centrifugation at 1,500 rpm for 5 min. Harvested cells were washed with PBS, re-suspended in 1.2 ml of PBS and 0.8 ml of lysis buffer (1.25% TritonX-100, 250 mM 2-mercaptoethanol (2-ME), and 50 mM EDTA in PBS) and lysed by vortexing for 30 sec. The lysates were then centrifuged at 3,000 rpm for 5 min at room temp and the supernatant was transferred to a 15 ml Falcon tube. The viruses were collected by centrifugation at 15,000 rpm for 20 min. The resultant pellets were then suspended in 0.33 ml of a nuclease solution (12.5 mM Tris-Cl (pH 7.5). 1 mg/ml DNase I and 1 mg/ml RNase A), incubated at 37° C. for 30 min, and disrupted by incubating at 55° C. for 30 min with 83 ml of SDS-protease solution (50 mM EDTA, 5% SDS, 0.5 mg/ml protease K, and 28.5 mM 2-mercaptoethanol). The obtained mixture was treated twice with phenol-chloroform, and NaCl was added to the aqueous phase to the final concentration of 0.2 M. The viral DNA was precipitated by adding 2.5 volumes of ice-cold ethanol, washed with 70% ethanol and subjected to centrifugation at 100,000×g for 5 min at 4° C. After air-drying, the pellets were dissolved in TE buffer (10 mM Tris-Cl (pH 8.0), 1 mM EDTA).

The viral DNA in TE buffer was digested with XhoI and SfuI and subjected to 0.8% agarose gel electrophoresis. The electrophoresed DNA fragments on the single gel were transferred simultaneously to two nylon membranes (Molecular Cloning: A Laboratory Manual, third edition, 6.35, Sambrook, J., and Russell, D. W. Cold Spring Harbor Laboratory). After fixing DNA by baking, the immobilized DNA was hybridized with DIG-labeled probe, "VP2 probe" or "IS45/46 probe", which were prepared with PCR DIG Probe Synthesis Kit (ROCHE DIAGNOSTICS, Cat. #1636090). VP2 probe was prepared with VP2-F (SEQ ID NO. 24) and VP2-R (SEQ ID NO. 25) as primers and p45/46bacVP2-E as a template. IS45/46 probe was prepared with 45/46-F (SEQ ID NO. 26) and 45/46-R (SEQ ID NO. 27) as primers and pNZ45/46Sfi as a template.

```
VP2-F
5'-CACCGTCCTCAGCTTACCCACATC-3'    (SEQ ID NO.24)

VP2-R
5'-ACGACGGATCCTGTTGCCACTCT-3'     (SEQ ID NO.25)

45/46-F
5'-GGGGAAGTCTTCCGGTTAAGGGAC-3'    (SEQ ID NO.26)

45/46-R
5'-GGTGCAATTCGTAAGACCGATGGG-3'    (SEQ ID NO.27)
```

The results of Southern blotting showed that a 4.7 kb fragment was hybridized to VP2 probe and 4.7 and 0.85 kb fragments to IS45/46 probe, indicating that the obtained rHVT/IBD-E had the expected genomic structure.

5.2. Stability of the Recombinant Virus rHVT/IBD-E was passaged twenty times in CEF cells and subjected to Southern blot analysis as described in EXAMPLE 5.1. The results were the same with those obtained in EXAMPLE 5.1, indicating that the recombinant virus was stable even after 20 passages

EXAMPLE 6

VP2 Gene Expression by the Recombinant Virus rHVT/IBD-E on the marrow of purification, after five passages in vitro, or wild-type HVT was propagated for 72 hours at 37° C. on $1 \times 10^7$ CEF cells in a 75-cm² flask to $1 \times 10^5$ pfu. Cells were recovered by scraping, transferred to a 15 ml Falcon™ tube and subjected to centrifugation at 2,000 rpm for 5 min. After washing with 10 ml of PBS, harvested cell pellets were suspended in 10 volumes of M-PER Mammalian Protein Extraction Reagent, supplied with Seize™ X Mammalian Immunoprecipitation Kit (Pierce, Cat #45225), transferred to an Eppendorf™ tube, kept at room temp for 10 min with brief mixings, and centrifuged at 2,000 rpm for 5 min. Next, the obtained supernatant was subjected to the affinity chromatography. The affinity column loaded with 1 mg of R63 monoclonal antibody was prepared with Seize™ X Mammalian Immunoprecipitation Kit as recommended by the supplier. Unbound proteins were eluted out and 20 ml of the bound protein fraction was supplemented with 5 ml of SDS-sample buffer that was included in the kit. The resultant mixture was then boiled for 5 min and subjected to 10% SDS-polyacrylamide gel electrophoresis. Briefly, the SDS-polyacrylamide gels were fixed with 50% methanol and 10% acetic acid solution and stained with 0.25% Coomassie Brilliant Blue R-250 (BIO-RAD) in 50% methanol and 10% acetic acid solution. Protein bands were visualized by destaining the gels with 50% methanol and 10% acetic acid solution. Two bands representing the immunoprecipitated VP2 protein were observed at 41 and 38-kilodaltons (kd) in the lanes of rHVT/IBD-E on the marrow of purification and after five passages (FIG. 5, Lane 2 and 3, respectively). By contrast, there was no band in the lane of wild-type HVT (FIG. 5 Lane 4). The 41-kd protein is the precursor protein and the 38-kd is the mature VP2 protein (A. A. Azad et al., 1987, Virology, 161:145–152, K. J., Fahey et al., 1985, J. Gen. Virol. 66:1479–1488).

EXAMPLE 7

Animal Trials 7.1. Animal Trial #1

The efficacy of rHVT/IBD-E as the IBD vaccine was evaluated by challenge testing using three different strains of IBDV serotype 1. First, 8,000 pfu of rHVT/IBD-E were inoculated into SPF embryonating chicken eggs at day 18 or subcutaneously into the nape of the newly born chicken. When three weeks old, vaccinated chickens were challenged intraocularly with $10^{3.5}$ EID$_{50}$/bird of IBDV STC, Delaware Variant E, or AL-2 strains. One week later, all chickens were weighed and necropsied to recover the Bursa of Fabricius, which were inspected for any lesions caused by Infectious Bursal Disease. The protection was evaluated by two criteria which are as follows. (1) The weight ratio of the bursa to the body (B/B index) was not statistically different from that of non-vaccinated, non-challenged chickens. (2) No malformation of the Bursa of Fabricius such as edematization, hemorrhage, yellowish exudate, discoloration, atrophy, or gelatinous exudate was detected. The results of Animal trial #1 were summarized in Table 3.

TABLE 3

Results of animal trial #1

| Vaccination | | | # Protected/total |
| --- | --- | --- | --- |
| Vaccine | Route | Challenge virus | (%) |
| rHVT/IBD-E | SQ | STC | 5/8 (63%) |
| rHVT/IBD-E | SQ | E | 8/8 (100%) |
| rHVT/IBD-E | SQ | AL-2 | 7/8 (88%) |
| rHVT/IBD-E | In ovo | STC | 5/9 (56%) |
| rHVT/IBD-E | In ovo | B | 7/9 (78%) |
| rHVT/IBD-E | In ovo | AL-2 | 8/9 (89%) |
| None | N/A | STC | 0/4 (0%) |
| None | N/A | E | 0/4 (0%) |
| None | N/A | AL-2 | 0/4 (0%) |
| None | N/A | None | 5/5 (100%) |

The IBDV challenge at three weeks of age is unusually severe. Nevertheless, more than 50% of all vaccinated chickens were protected against the challenge with E, STC or AL-2 IBDV strains, indicating that rHVT/IBD-E can induce protective immunity in chickens against a variety of different subtypes of IBDV.

7.2. Animal Trial #2

As shown in EXAMPLE 4.2, rHVT/IBD-STC#11 comprises VP2 cDNA derived from STC, a classical virulent strain. The efficacy of rHVT/IBD-STC#11 as the IBD vaccine was evaluated similarly as in EXAMPLE 7.1. As shown in Table 4, 90% of chickens subcutaneously vaccinated with rHVT/IBD-STC#11 were protected against the challenge with STC but only 30% to 50% against the challenge with AL-2, a different subtype of IBDV. Taking Table 3 into consideration, rHVT/IBD-E was far superior to rHVT/IBD-STC#11.

TABLE 4

Results of animal trial #2

| Vaccination | | | #Protected/total |
|---|---|---|---|
| Vaccine | Route | Challenge virus | (%) |
| rHVT/IBD-STC#11 | SQ | STC | 9/10 (90%) |
| rHVT/IBD-STC#11 | SQ | E | 7/10 (70%) |
| rHVT/IBD-STC#11 | SQ | AL-2 | 3/10 (30%) |
| rHVT/IBD-STC#11 | In ovo | STC | 9/10 (90%) |
| rHVT/IBD-STC#11 | In ovo | E | 7/10 (70%) |
| rHVT/IBD-STC#11 | In ovo | AL-2 | 5/10 (50%) |
| None | N/A | STC | 0/5 (0%) |
| None | N/A | E | 0/5 (0%) |
| None | N/A | AL-2 | 0/5 (0%) |
| None | N/A | None | 5/5 (100%) |

EXAMPLE 8

Animal Trial #3

The efficacy of rHVT/IBD-E and rHVT/IBD-STC#11 as the IBD vaccine was evaluated in maternal antibody positive chickens. At two days of age, Dekalb TX chickens (Ise Farm, Japan) were vaccinated subcutaneously with 2,200 pfu/bird of rHVT/IBD-E or of rHVT/IBD-STC#11. 40 days post vaccination and at six weeks of age, the vaccinated chickens were challenged with 103 EID50/bird of STC. One week later, all chickens were weighed and necropsied to recover the Bursa of Fabricius, which were inspected for any lesions caused by Infectious Bursal Disease. The protection was evaluated by the B/B index and malformation of the Bursa of Fabricius. The results are summarized in Table 5.

As the control commercial live IBD vaccine Kaketsuken K (Chemo-Sero-Therapeutic Research Institute, Japan) was administered to 10 day old chickens as recommended by the supplier. Maternal antibodies at 2 days of age were titrated by a commercial ELISA kit, Flock Check Infectious Bursal Disease Antibody Test Kits (IDEXX Laboratory, Inc.). The averaged S/P value was 1.2, indicating that the maternal antibody level of tested chickens was very high.

TABLE 5

Results of animal trial #3

| | | | | | IBD Challenge | | |
|---|---|---|---|---|---|---|---|
| | Group | Actual Dose/chick | Route | # of chickens | Pro/T | % Protected | B/B ratio |
| 1 | Challenge controls | N/A | N/A | 20 | 0/20 | 0 | 2.13 ± 0.13 |
| 2 | Non challenge controls | N/A | N/A | 10 | 10/10 | 100 | 5.09 ± 0.25 |
| 3 | rHVT/IDB-E | 2200 | SC | 20 | 18/20 | 90 | 4.69 ± 0.27 |
| 4 | rHV/STC#11 | 2200 | SC | 20 | 20/21 | 95 | 5.06 ± 0.27 |
| 5 | Live vaccine | On label | On label | 20 | 14/21 | 67 | 3.91 ± 0.16 |

The results summarized in Table 5 indicate that both of rHVT/IBD-E and rHVT/IBD-STC#11 conferred more than 90% protective immunity on chickens that had high levels of IBDV maternal antibody. rHVT/IBD-E was proven to be an excellent IBD vaccine which was efficacious against the challenge with STC, belonging to the different subtype from that of E, from which the inserted VP2 gene of rHVT/IBD-E was originated.

What is claimed is:

1. An avian recombinant herpesvirus comprising cDNA under the control of the chicken beta-actin promoter wherein the said cDNA encodes VP2 of the Delaware Variant E strain of IBDV and is inserted into a region of the avian herpesvirus genome which is non-essential for virus growth.

2. An avian recombinant herpesvirus as in claim 1 wherein the sequence of the chicken beta-actin promoter is that shown in SEQ ID NO.3.

3. An avian recombinant herpesvirus as in claim 1 wherein the cDNA is inserted into the non-translated intergenic region between the UL45 and UL46 genes of the herpesvirus genome.

4. A poultry vaccine comprising the avian recombinant herpesvirus as in claim 1 wherein the said vaccine confers on chickens 50% or more of protection against the challenge of a variety of different subtypes of infectious bursal disease virus.

* * * * *

UNITED STATES PATENT AND TRADEMARK OFFICE
CERTIFICATE OF CORRECTION

PATENT NO.    : 6,764,684 B2
DATED         : July 20, 2004
INVENTOR(S)   : Takanori Sato et al.

It is certified that error appears in the above-identified patent and that said Letters Patent is hereby corrected as shown below:

Title page,
Item [75], Inventors, change "Shuji Saitoh, Kanagawa (JP); Takashi Okuda, Tokyo (JP); Mayumi Kubomura, Kanagawa (JP); Kristi M. Moore, Lenexa, KS (US)" to be -- Takanori Sato, Kanagawa (JP); Yoshinari Tsuzaki, Kanagawa (JP); Motoyuki Esaki, Lenexa, KS (US); Kristi M. Dorsey, Lenexa, KS (US) --

Signed and Sealed this

Fifth Day of October, 2004

JON W. DUDAS
*Director of the United States Patent and Trademark Office*